US00PP13210P3

(12) United States Plant Patent
Zary

(10) Patent No.: US PP13,210 P3
(45) Date of Patent: Nov. 12, 2002

(54) FLORIBUNDA ROSE PLANT NAMED 'JACNEREB'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 11 days.

(21) Appl. No.: 09/779,325

(22) Filed: Feb. 7, 2001

(65) Prior Publication Data

US 2002/0108156 P1 Aug. 8, 2002

(51) Int. Cl.[7] ..... A01H 5/00

(52) U.S. Cl. ..... Plt./143

(58) Field of Search ..... Plt./143

*Primary Examiner*—Bruce R. Campell
*Assistant Examiner*—Susan B. McCormick
(74) *Attorney, Agent, or Firm*—Klarquist Sparkman, LLP

(57) ABSTRACT

A floribunda rose plant characterized by its compact, well-branched but vigorous growth; its dark green, disease resistant foliage; and its large, cupped, old fashioned looking flowers having a high petal count and a strong, sweet, fruity fragrance.

1 Drawing Sheet

LATIN NAME OF GENUS AND SPECIES

*Rosa hybrida.*

VARIETY DENOMINATION

'JACnereb'.

SUMMARY OF THE INVENTION

The present invention relates to a new and distinct variety of rose plant of the floribunda class which was originated by me by crossing the variety 'JACdew', U.S. Plant Pat. No. 5,122, with the variety 'HARrooney', U.S. Plant Pat. No. 5,582.

BACKGROUND OF THE INVENTION

The primary objective of this breeding was to produce a new rose variety having the dark green disease resistant foliage and compact, vigorous plant of the female parent combined with the large flower and sweet fragrance of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Strong, sweet, fruity fragrance;
2. Compact, well-branched plant;
3. Dark green, disease resistant foliage;
4. Large, cupped, old fashioned looking flower;
5. High petal count; and
6. Vigorous growth.

Asexual reproduction of this new variety by budding on 'Dr. Huey' understock (unpatented), as performed at Wasco, Calif., shows that the foregoing and all other characteristics and distinctions come true to form and are established and transmitted through succeeding propagations.

COMPARISON WITH PARENTS

'JACdew', the female parent, is an orange floribunda having 3½ inch flowers with a slight fragrance. The flowers having 10–15 petals per bloom. 'HARrooney', the male parent, is an amber-yellow floribunda with 20–30 petals having a strong fragrance, the flowers being 4–4½ inches in diameter. 'JACnereb' has peach-apricot colored flowers that are 4 inches in diameter and have 40–45 petals with a strong fruity fragrance.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (1966), except where ordinary dictionary significance of color is indicated.

Parentage:
*Seed parent.*—'JACdew'. (U.S. Plant Pat. No. 5,122).
*Pollen parent.*—'HARrooney'. (U.S. Plant Pat. No. 5,582).

Classification:
*Botanical.*—*Rosa hybrida.*
*Commercial.*—Floribunda.

FLOWER

Observations made from specimens beginning at two years of age grown in a garden environment at Somis, Calif. in March, 1999 to November, 2000.

Blooming habit: Continuous.

Bud:

*Size.*—One and one-quarter inch long, 1¼–1½ inches in diameter when the petals start to unfurl.

*Form.*—The bud form is long, pointed ovoid.

*Color.*—When sepals first divide, bud color is Yellow-Orange Group 23D changing to a blush of Red Group 41D on the upper third of the bud. The very tip of the bud is Red Group 41C. When half blown, the upper sides of the petals are Yellow-Orange Group 23D on the outer petals. The inner petals are Yellow-Orange Group 23D blushed with Red Group 41D toward the outer thirdof the petal with an edge of Red Group 41C; and the lower sides of the petals are Yellow-Orange Group 23D with a blush of Red Group 41D on the petal edge.

*Sepals.*—Color: Green Group 138B. Length: 1⅛ inch–1 3/16 inch. Width: 9/16 inch–¾ inch. Surface texture: Covered in fine hairs. There are three lightly appendaged sepals. There are two unappendaged sepals with hairy edges.

*Receptacle.*—Color: Green Group 138C. Shape: Funnel. Size: Length: 3/16 inch. Width: ¼ inch. Surface: Smooth.

*Peduncle.*—Length: Short, averaging about 2 inches. Surface: Smooth with a few glands. Color: Green Group 138D. Strength: Stiff, erect.

Bloom:

*Size.*—Average open size is 4 inches.

*Borne.*—Singly and several together in pyramidal clusters of 3 to 5 blooms.

*Stems.*—Strength: Strong. Average length is about 12 to 14 inches. Average diameter is about 5/16 inch.

*Form.*—When first open: Globular to cupped. Permanence: All petals curl back.

*Petalage.*—Number of petals under normal conditions: 40 to 45.

*Color.*—The upper sides of the petals are Yellow-Orange Group 23D on the outer petals. The inner petals are Yellow-Orange Group 23D blushed with Red Group 41D toward the outter third of the petal. The edge of the petal is Red Group 41C. The reverse sides of the petals are Yellow-Orange Group 23D with a blush of Red Group 41D on petal edge. The base of each petal has a small (3/16"×3/16") Yellow Group 6C color spot. The major color on the upper side is Yellow-Orange Group 23D.

*Variegations.*—None.

*Discoloration.*—The general tonality at the end of the first day: No change. At the end of the third day: No change. By day six there is a general fading in color to Orange Group 27B. This is followed by petal drop on day seven or eight.

*Fragrance.*—Strong, fruity.

Petals:

*Texture.*—Coriaceous.

*Size.*—Length: 1 inch. Width: 1 inch.

*Shape.*—Round to deltoid. Base Shape: Cuneate. Apex Shape: Obcordate.

*Form.*—Tips slightly recurved.

*Arrangement.*—Imbricated. Petaloids in the center are few (three to five), ¼"–½" inch long, ⅛"–⅜" wide with color similar to that of petals.

*Persistence.*—Petals drop off cleanly before drying.

*Lastingness.*—On the plant: Fair (about six or seven days). As a cut flower: Fair (about seven days).

Reproductive parts:

*Anthers.*—Size: 1/32 inch. Quantity: 160–200. Color: Yellow-Orange Group 16D. Arrangement: Regular round styles.

*Filaments.*—Color: Yellow-Orange Group 16C. Length: 3/16 inch.

*Pollen.*—Color: Yellow-Orange Group 22D.

*Hips.*—None observed.

*Styles.*—Color: Green-White Group 157B at the base and on the upper one-fourth Red Group 51C. Length: ⅛ inch.

*Stigmas.*—Color: Yellow-White Group 158B.

Plant:

*Form.*—Bush.

*Growth.*—Vigorous, upright, branching. At maturity, height is 3½ feet, width is 2½ feet after one full season of growth in Somis, Calif.

Foliage: Number of leaflets on normal mid-stem leaves: 5 or 7.

*Size.*—Medium (5 inches long×4 inches wide).

*Quantity.*—Abundant.

*Color.*—New foliage. Upper surfaces: Green Group 137B edged in Greyed-Orange Group 176B. Lower side: Green Group 137B edged in Greyed-Orange Group 176B. Old foliage: Upper surface: Green Group 136A. Lower surface: Green Group 136B.

Leaflets:

*Shape.*—Pointed oval. Length: 1¾ inches–2 inches. Width: 1–1¼ inch.

*Texture.*—Leathery, glossy.

*Edge.*—Serrated.

*Serration.*—Single, small.

*Petiole rachis.*—Color: Green Group 139B.

*Petiole.*—Length: 1⅙ inch. Diameter: 3/64 inch.

*Petiole underside.*—Rough with prickles.

*Stipules.*—Medium. serrated (about ½ inch).

*Disease resistance.*—Resistant to mildew and rust, susceptible to blackspot under normal growing conditions.

*Venation pattern.*—Costate.

*Vein color.*—Green Group 139B.

Wood:

*New wood.*—Color: Green Group 137B. Bark: Smooth.

*Old wood.*—Color: Green Group 137B. Bark: Smooth.

Prickles:

*Quantity.*—On main canes from base: Many. On laterals from main canes: Ordinary.

*Form.*—Medium, straight, hooked downward. Length: ¼ inch. Width: 3/16 inch.

*Color when young.*—Greyed-Red Group 179C.

*Color when mature.*—Grened-Orange Group 171D to Greyed-Yellow Group 161D.

Small prickles:

*Quantity.*—On main stalks: Few. On laterals: None on laterals.

*Color.*—Greyed-Red Group 179C.

I claim:

1. A new and distinct variety of floribunda rose plant as herein shown and described, characterized particularly as to novelty by its compact, well-branched but vigorous growth; its dark green, disease resistant foliage; and its large, cupped, old fashioned looking flowers having a high petal count and a strong, sweet, fruity fragrance.

* * * * *

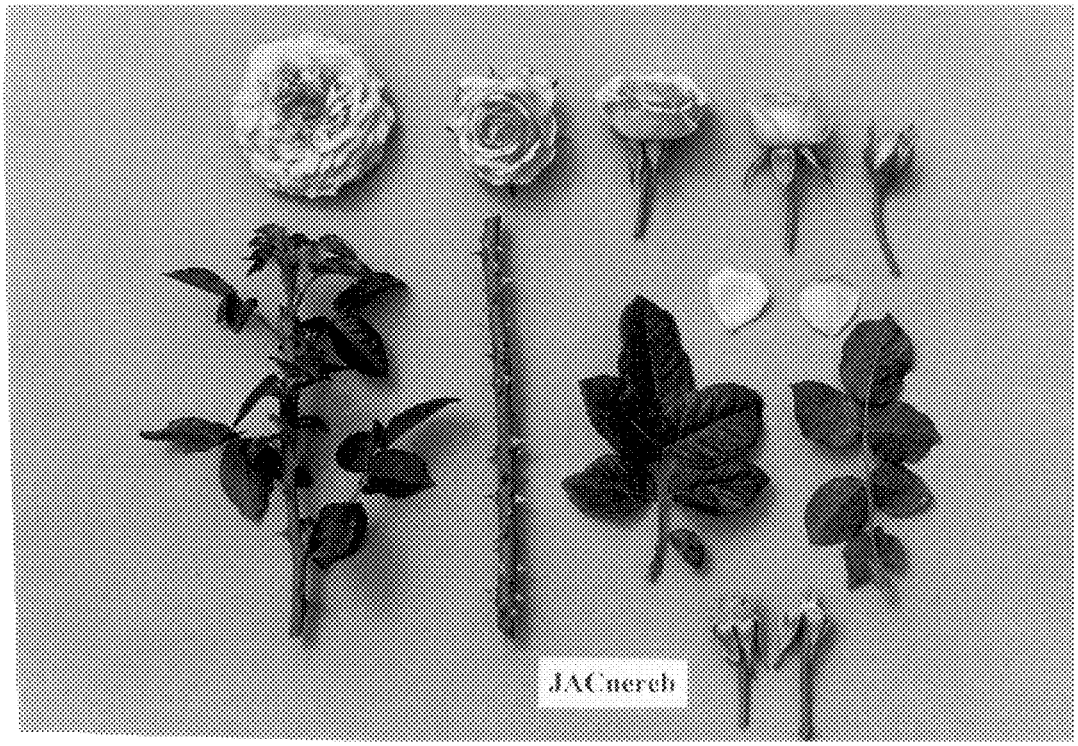
JACnerch

UNITED STATES PATENT AND TRADEMARK OFFICE

CERTIFICATE OF CORRECTION

PATENT NO. : PP 13,210 P2
DATED : November 12, 2002
INVENTOR(S) : Keith W. Zary

It is certified that error appears in the above-identified patent and that said Letters Patent is hereby corrected as shown below:

Column 3,
Line 13, "thirdof" should be -- third of --
Line 41, "outter" should be -- outer --

Column 4,
Line 51, "Grened" should be -- Greyed --

Signed and Sealed this

Second Day of December, 2003

JAMES E. ROGAN
*Director of the United States Patent and Trademark Office*